US008652632B2

(12) United States Patent
Demirel et al.

(10) Patent No.: US 8,652,632 B2
(45) Date of Patent: *Feb. 18, 2014

(54) SURFACE ENHANCED RAMAN DETECTION ON METALIZED NANOSTRUCTURED POLYMER FILMS

(75) Inventors: Melik C. Demirel, State College, PA (US); Walter J. Dressick, Waldorf, MD (US); David Allara, State College, PA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 126 days.

This patent is subject to a terminal disclaimer.

(21) Appl. No.: 12/477,394

(22) Filed: Jun. 3, 2009

(65) Prior Publication Data

US 2009/0257056 A1 Oct. 15, 2009

Related U.S. Application Data

(63) Continuation-in-part of application No. 12/108,549, filed on Apr. 24, 2008.

(60) Provisional application No. 60/913,574, filed on Apr. 24, 2007, provisional application No. 61/058,275, filed on Jun. 3, 2008.

(51) Int. Cl.
*B32B 3/26* (2006.01)
*C23C 14/20* (2006.01)

(52) U.S. Cl.
USPC .............. 428/319.1; 428/315.5; 428/375; 977/762; 427/597; 427/443.1; 427/255.6

(58) Field of Classification Search
USPC ......... 428/317.9, 375, 315.5, 319.1; 977/762; 427/597, 443.1, 255.6
See application file for complete search history.

(56) References Cited

U.S. PATENT DOCUMENTS

| 3,011,920 A | 12/1961 | Shipley |
| 4,005,238 A | 1/1977 | Gaehde et al. |
| 5,104,480 A | 4/1992 | Wojnarowski et al. |
| 5,866,430 A | 2/1999 | Grow |
| 2001/0039043 A1 | 11/2001 | Lihme et al. |
| 2003/0217928 A1* | 11/2003 | Lin et al. ............... 205/109 |
| 2004/0146560 A1* | 7/2004 | Whiteford et al. ........ 424/484 |

(Continued)

FOREIGN PATENT DOCUMENTS

WO 2005108460 A1 11/2005

OTHER PUBLICATIONS

Chen et al., "A Non-Covalent Approach for Depositing Spatially Selective Materials on Surfaces" Ad. Funct. Mater., 15, 1364-1375 (2005).*

(Continued)

*Primary Examiner* — Hai Vo
(74) *Attorney, Agent, or Firm* — US Naval Research Laboratory; Joseph T. Grunkmeyer

(57) ABSTRACT

Disclosed herein is a structure having a spatially organized polymer nanostructured thin film and a metal coating on the film. The thin film is made by directing a monomer vapor or pyrolyzed monomer vapor towards a substrate at an angle other than perpendicular to the substrate, and polymerizing the monomer or pyrolyzed monomer on the substrate.

29 Claims, 11 Drawing Sheets

(56) References Cited

U.S. PATENT DOCUMENTS

| | | | |
|---|---|---|---|
| 2005/0227055 A1 | 10/2005 | Senkevich et al. | |
| 2005/0265648 A1* | 12/2005 | Roitman et al. | 385/12 |
| 2006/0159916 A1 | 7/2006 | Dubrow et al. | |
| 2006/0207878 A1 | 9/2006 | Myung et al. | |
| 2006/0252065 A1 | 11/2006 | Zhao et al. | |
| 2006/0257968 A1 | 11/2006 | Van Duyne et al. | |
| 2007/0166539 A1 | 7/2007 | Zhao et al. | |
| 2008/0144026 A1 | 6/2008 | Zhao et al. | |
| 2008/0268226 A1 | 10/2008 | Demirel et al. | |
| 2010/0060109 A1* | 3/2010 | Russell et al. | 310/363 |

OTHER PUBLICATIONS

Pursel et al., "Growth of Sculptured Polymer Submicrowire Assemblies by Vapor Deposition" Polymer, 46, 9544-9548 (2005).*
Office action in U.S. Appl. No. 12/108,549 (Apr. 22, 2011).
Office action in U.S. Appl. No. 12/108,549 (Nov. 12, 2010).
Office action in U.S. Appl. No. 12/108,549 (May 4, 2010).
Office action in U.S. Appl. No. 12/108,549 (Oct. 13, 2011).
Office action in U.S. Appl. No. 12/108,549 (May 31, 2012).
Office action in U.S. Appl. No. 12/430,932 (Jun. 27, 2012).
Office action in U.S. Appl. No. 12/108,549 (May 3, 2013).
Kostelansky et al., "Triarylphosphine-Stabilized Platinum Nanoparticles in Three-Dimensional Nanostructured Films as Active Electrocatalysts" J. Phys. Chem. B, 2006, 110 (43).
Kao et al., "Surface-Enhanced Raman Detection on Metalized Nanostructured Poly(p-xylene) Films" Adv. Mater. 2008, 20, 3562-3565.
Dressick et al., U.S. Appl. No. 12/430,932, (Jun. 27, 2012).
Cetinkaya et al., "Growth of nanostructured thin films of poly(p-xylylene) derivatives by vapor deposition" Polymer, xx, (2007), p. 1-5.
PCT Search Report and Written Opinion in PCT/US09/46084, Aug. 7, 2009.

* cited by examiner

SURFACE ENHANCED RAMAN DETECTION ON METALIZED NANOSTRUCTURED POLYMER FILMS

This application is a continuation-in-part application of U.S. patent application Ser. No. 12/108,549, filed on Apr. 24, 2008, which claims priority to U.S. Provisional Patent Application No. 60/913,574, filed on Apr. 24, 2007. This application claims the benefit of U.S. Provisional Application No. 61/058,275, filed on Jun. 3, 2008. These applications and all other publications and patent documents referred to throughout this nonprovisional application are incorporated herein by reference.

TECHNICAL FIELD

The present disclosure is generally related to substrates for use with surface enhanced Raman spectroscopy (SERS) and other techniques.

DESCRIPTION OF RELATED ART

Surface enhanced Raman spectroscopy (SERS) as a basis of rapid and reliable biosensing techniques can have the advantages of minimal sample preparation and ease of operation compared to other methods. The SERS technique has received much attention over the years due to its ability to reach single molecule detection and for applications such as rapid DNA sequencing. Its use for biomedical analysis, however, has lagged because of the difficulties in finding effective substrates for accommodating biological entities which also provide high sensitivity and highly reproducible SERS responses from sample to sample. If these challenges are met, SERS could potentially be extremely useful in the field of medical diagnostics to detect infectious agents.

The phenomena of surface enhanced Raman was first observed in 1974 (Fleischmann et al., "Raman-Spectra of Pyridine Adsorbed at a Silver Electrode" *Chem. Phys. Lett.,* 26(2), 163-166 (1974)) on an electrochemically roughened silver substrate using pyridine as an analyte. Since then the technique of SERS has received much attention due to its capability for single molecule detection and a variety of applications including rapid DNA sequencing (Kneipp et al., "Detection and identification of a single DNA base molecule using surface-enhanced Raman scattering (SERS)" *Physical Review E,* 57(6), R6281-R6284 (1998)), pathogen detection (Farquharson et al., "Detection of bioagent signatures: a comparison of electrolytic and metal-doped sol-gel surface-enhanced Raman media. in Chemical and Biological Early Warning Monitoring for Water, Food, and Ground" SPIE, Boston, Mass. (2002); Shanmukh et al., "Rapid and sensitive detection of respiratory virus molecular signatures using a silver nanorod array SERS substrate" *Nano Letters,* 6(11), 2630-2636 (2006), nanostructure characterization (Lefrant et al., "Surface-enhanced Raman scattering studies on chemically transformed carbon nanotube thin films" *J. Roman Spectroscopy,* 36(6-7), 676-698 (2005)), and food analysis (Peica et al., "Vibrational characterization of E102 food additive by Raman and surface-enhanced Raman spectroscopy and theoretical studies" *J. Roman Spectroscopy,* 36(6-7), 657-666 (2005)). One of the most promising broad based applications for advanced, high quality SERS substrates would be in the field of diagnostic microbiology (Zeiri et al., "Surface-enhanced Raman spectroscopy as a tool for probing specific biochemical components in bacteria" *Applied Spectroscopy,* 58(1), 33-40 (2004); Vo-Dinh et al., "Surface-enhanced Raman scattering for medical diagnostics and biological imaging" *J. Roman Spectroscopy,* 36(6-7), 640-647 (2005); Doering et al., "SERS as a foundation for nanoscale, optically detected biological labels" *Advanced Materials,* 19(20), 3100-3108 (2007)) with critical application such as the detection of bacterial and viral pathogens where minimal sample preparation effort, low reagent costs and ease of operation and rapid and reliable detection would offer a great advantage compared to traditional culture or amplification based techniques (Belgrader et al., "Infectious disease—PCR detection of bacteria in seven minutes" *Science,* 284(5413), 449-450 (1999)). Some demonstrations of SERS detection have been reported for microorganism detection using gold nanoparticle coated $SiO_2$ (Premasiri et al., "Vibrational fingerprinting of bacterial pathogens by surface enhanced Raman scattering (SERS)" in Chemical and Biological Sensing VI. Orlando, Fla., USA: SPIE (2005)), bacteria coated with deposited silver coatings (Efrima et al., "Surface-enhanced Raman spectroscopy of bacteria coated by silver" in Advances in Fluorescence Sensing Technology IV. San Jose, Calif., USA: SPIE (1999)), co-deposited bacteria and silver on inert substrates (Jarvis et al., "Discrimination of bacteria using surface-enhanced Raman spectroscopy" *Analytical Chemistry,* 76(1), 40-47 (2004)), and bacteria treated with reducing agent for the formation of metal colloids (Zeiri et al., "Silver metal induced surface enhanced Raman of bacteria" *Colloids and Surfaces a—Physicochemical and Engineering Aspects,* 208 (1-3), 357-362 (2002)). SERS has remarkable analytical sensitivity but practical diagnostic SERS probes have not been developed due to the difficulty in preparing robust and uniform SERS substrates of correct surface morphology (i.e., nanoscale roughness) and metal particle distribution that provide maximum SERS enhancement.

BRIEF SUMMARY

Disclosed herein is a structure comprising: a spatially organized polymer nanostructured thin film; and a metal coating on the film. The thin film is made by a method comprising: directing a monomer vapor or pyrolyzed monomer vapor towards a substrate at an angle other than perpendicular to the substrate; and polymerizing the monomer or pyrolyzed monomer on the substrate.

Also disclosed herein is a method comprising: providing a spatially organized polymer nanostructured thin film; and depositing a metal coating on the film. The thin film is made by the method described above.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein are SERS substrates that may provide a highly uniform and reproducible bioanalysis surface and examples of "fingerprint" signals from different bacteria types in which the signals differ based on variations in the cell membranes. The substrates are hybrid metal-organic layered thin film structures having controlled surface roughness which may result in reproducible and uniform (i.e., ±5% over >1 mm area) surface-enhanced Raman spectroscopy (SERS) signals for analysis of materials bound to the metal portion of the film. A potential advantage of using these substrates is that no template or lithography is involved, thus providing a simple, inexpensive and quick method to achieve highly sensitive and spatially uniform SERS signal for biomedical applications.

Figure 1:
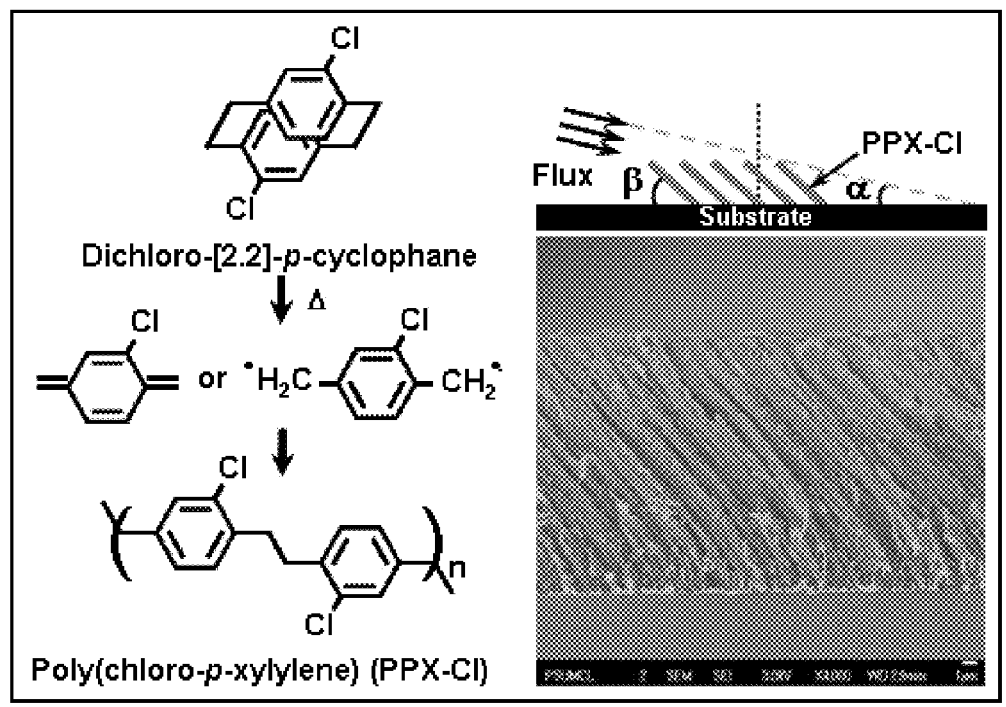
FIG. 1 illustrates nanostructured PPX preparation.

First, nanostructured polymer films, such as poly(p-xylylene) (PPX), are prepared using an oblique angle polymerization method (Pursel et al., "Growth of sculptured polymer submicronwire assemblies by vapor deposition" *Polymer,* 46(23), 9544-9548 (2005); Boduroglu et al., "Controlling the Wettability and adhesion of nanostructured poly-(p-xylylene) films" *Langmuir,* 23(23), 11391-11395 (2007); Cetinkaya et al., "Growth of nanostructured thin films of poly (p-xylylene) derivatives by vapor deposition" *Polymer,* 48(14), 4130-4134 (2007); Demirel et al., "Noncovalent deposition of nanoporous Ni membranes on spatially organized poly(p-xylylene) film templates" *Advanced Materials,* 19(24), 4495-4499 (2007); US Patent Application Publication Nos. 2007/0148206 and 2008/0268226; U.S. patent application Ser. No. 12/430,932). The film may consist of a parallel assembly of nanowire arrays having a diameter of ~150 nm and column size (i.e., film thickness) of ~10-50 μm inclined at an angle other than a right angle with respect to the substrate. FIG. 1 illustrates nanostructured PPX preparation. The nanowires may be straight columns (made by not rotating the substrate during film deposition) or have other shapes. Suitable monomers include, but are not limited to, a [2.2]-cyclophane, dichloro-[2.2]-cyclophane, an amino-[2.2]-cyclophane, a diamino-[2.2]-cyclophane, an aminomethyl-[2.2]-cyclophane, a trifluoroacetyl[2.2]-cyclophane, and dibromo-[2.2]-cyclophane. These monomers are vapor-phase pyrolyzed to form a poly-p-xylylene on the substrate, as described in the above references.

Second, a metal coating, such as one or more SERS-active metals (e.g., Au, Ag, Cu, Ni, Pt), or surface enhanced resonance Raman spectroscopy-active metals are deposited onto the nanostructured polymer, which can result in hybrid metal-organic "layered" SERS active films with high sensitivity and reproducibility that can serve as biosensing surfaces. Metal deposition may be performed using thermal evaporation methods. Electroless deposition or sputtering of the SERS active metal and other methods described herein provide alternative methods for creating the metal film.

Another alternative for metal film fabrication involves galvanic displacement. In this process, the electroless or thermal deposition of a less-noble metal, such as a SERS-inactive or weakly SERS-active metal, Ni, Co, Fe, or Cu, is followed by treatment of the freshly deposited metal film with a solution containing ions of the more noble, SERS-active metal (e.g., Ag(I), Au(III), Pt(II)). (Note that copper may be displaced even though it is SERS-active.) The ions of the more noble SERS-active metal are spontaneously reduced at the surface of the less noble metal film, oxidizing the less noble metal atoms on the surface and depositing a thin film of noble metal upon the less noble metal surface. The reaction proceeds spontaneously until the entire surface of the less noble metal film is covered by a thin layer of the more noble metal. The result is a composite layered metal film comprising a thin outermost layer of the SERS-active noble metal covering the underlying less noble metal film, which in turn covers the nanostructured poly-p-xylylene film. For example, deposition of a Ni film onto the nanostructured poly-p-xylylene thin film, followed by treatment with a solution containing Au(III) ions, leads to oxidation of the surface Ni metal atoms to Ni(II) ions, which are released into the solution. At the same time, Au(III) ions are spontaneously reduced to Au metal atoms, which deposit onto the Ni film surface. The reaction proceeds until the entire Ni surface is covered by a thin Au metal film, producing a Au—Ni layered metal film atop the nanostructured PPX film.

The metal coating may also be applying by the method disclosed in US Patent Application Publication No. 2008/0268226. In this method a ligand adsorbate is adsorbed onto the thin film. A Pd catalyst is then bound to the ligand adsorbate adsorbed onto the thin film. Finally one or more metal layers or metal nanoparticles are deposited, overlaying the Pd catalyst bound to the ligand adsorbate. For example, the ligand adsorbate may be adsorbed by exposing the thin film to a pyridine solution or vapor. The Pd catalyst may be bound by exposing the thin film to a Pd catalyst. The metal layers may be deposited by exposing the thin film to an electroless silver, gold, copper, nickel, or platinum bath.

In another method, a colloidal Pd/Sn catalyst is bound to the polymer film. The catalyst comprises Sn-coated Pd particles. A portion of the Sn is then removed by treatment with hydrochloric acid. This may then be followed by treatment with an accelerator such as fluoroboric acid, followed by depositing one or more metal layers overlaying the Pd/Sn catalyst. This deposition may be by exposing the thin film bearing the Pd/Sn catalyst to an electroless silver, gold, copper, nickel, or platinum bath.

In another method, a layer of one or more ferromagnetic metals is deposited by e-beam deposition on the metal coating. In another method, a layer of chromium or titanium is applied onto the polymer before depositing the metal coating. Chromium or titanium can generally not be exchanged with a more noble metal as described above.

The substrate may be used by exposing it to a sample suspected of containing an analyte, and performing a surface enhanced Raman spectroscopy analysis or a surface enhanced resonance Raman spectroscopy analysis of the exposed structure. Methods of performing these analyses are known in the art. The analyte may be any material that may be detected by these methods including, but not limited to, organic or inorganic molecules, macromolecules derived from a biological source, engineered macromolecules derived from a chemical or biological source, proteins, antibodies, lipids, polysaccharides, nucleic acids, membranes, organelles of a cell, viruses, bacteria, protozoa, or cells from a multicellular or unicellular organism. The analyte may be in liquid or solution form, an aerosol, or a dust particle. The analyte may also be a living virus, bacterium, protozoan, or cell. Applications include, but are not limited to, biomedical sensing and characterization of microorganisms, monitoring industrial processes, gene-function analysis for metabolic footprint, and low concentration detection of hazardous and toxic substances. The high spatial uniformity and reproducibility of SERS signal, at millimeter length scales is suitable for bacterial detection. Thus, the SERS technique potentially provides a non-invasive and non-destructive method for bacterial analysis without amplification of cultures and with the capability of a re-usable, inexpensive, and easily fabricated substrate.

Figure 2:
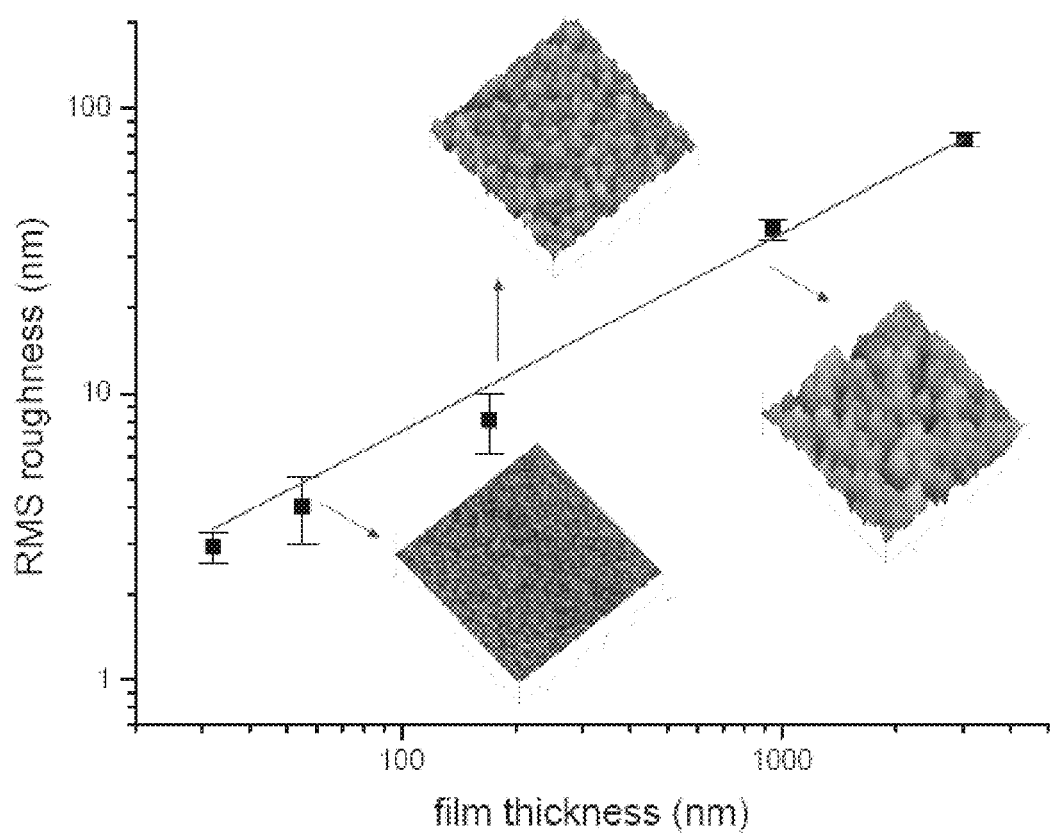
FIG. 2 shows the rms surface roughness of a PPX film as a function of polymer film thickness. The scale bars for the AFM scans are X:1 µm/div, Y:1 µm/div, Z:300 nm/div.

The nanostructured substrate may provide a significant advantage over traditional SERS surfaces because the surface roughness of nanostructured PPX film can be controllable over two length scales in the ~10 nm and 100 μm regimes. FIG. 2 shows the rms surface roughness of a PPX film as a function of polymer film thickness. The increase in surface roughness as the film becomes thicker is inherent to oblique angle polymerization. Additionally, this technique does not require any template or lithography for its preparation; thus making it simple and quick method to prepare uniform nanostructured SERS active films. Proper selection of the deposition geometry and conditions, and the PPX derivative permits simultaneous control of film morphology, topology, and surface chemistry, yielding nanostructured PPX films having well-organized porous structures.

A non-invasive and non-destructive method for bacterial analysis without amplification of cultures may be provided through the use of the hybrid metal-organic composite structures described herein. These SERS substrates may be reusable and inexpensive as well as easy to fabricate. In the case of gold the substrate may be highly cleanable for continued use in operator independent situations. The results described in the examples below show clear differentiation between Gram-positive and Gram-negative bacterial species. The potential for SERS to produce spectra that can be used for rapid whole-organism fingerprinting is extremely important for outbreak prediction, reducing the mortality rate from misdiagnosis of infectious diseases in hospital as well as understanding the fundamental strain epistemology in infectious diseases.

The following examples are given to illustrate specific applications. These specific examples are not intended to limit the scope of the disclosure in this application.

Example 1

Materials:

All chemicals were A.C.S reagent grade and were used as received. Deionized water of 18.1 MΩ-cm was used for all experiments using Barnstead Nanopure Diamond™ dispenser. Poly(chloro-p-xylylene) (PPX-Cl) films were prepared from dichloro-[2,2]paracyclophane (DCPC), which was purchased from Parylene Distribution Services and deposited on p-type Si (100) wafers (Wafernet Inc. San Jose, Calif.).

Structured PPX-Cl Film Preparation:

Silicon wafers were first sonicated in acetone. Afterwards, the wafers were washed in water and dried using nitrogen gas. The wafers were then transferred to a 1:1 (volume) solution of HCl and methanol. After 30 minutes, the wafers were removed and washed with copious amounts of water and dried under nitrogen gas. The wafers were then kept in concentrated sulfuric acid for another 30 minutes after which they were washed and sonicated in water for 10 minutes. The wafers were thoroughly dried under nitrogen gas. The self assembled monolayer (SAM) solution was prepared by adding 1% allyltrimethoxysilane (Gelest, Pa.) in toluene containing 0.1% acetic acid. The cleaned wafers were transferred to this solution and left for SAM formation for 60 minutes at 25° C. The wafers were removed after 60 minutes and sonicated in anhydrous toluene for 10 minutes. The wafers were then dried on a hot plate at 140° C. for 5 minutes for solvent removal. Nanostructured PPX-Cl films were deposited on the wafers using 0.3 g of DCPC. The vaporizer and the pyrolysis chamber temperatures were maintained at 175° C. and 690° C. respectively. The angle between the substrate and the flux was held constant at 10° during the deposition for all the samples.

Metal Deposition:

The preparation of substrate for SERS experiment was started from the structured poly(chloro-p-xylylene) film templates. The gold and silver were thermal deposited from resistively-heated tungsten and tantalum boats onto the surface at about $1\times10^{-8}$ torr base pressure in a cryogenically pumped deposition chamber. The thickness of gold deposition was determined by a parallel QCM.

The deposited metal films (100, 300 and 600 Å) were immersed into 1 mM fluorobenzenethiol (FBT) solution for 24 hours. After that, the sample was rinsed with pure ethanol for 1 min to remove additional physical adsorbed FBT then dried under nitrogen gas.

Figure 3:
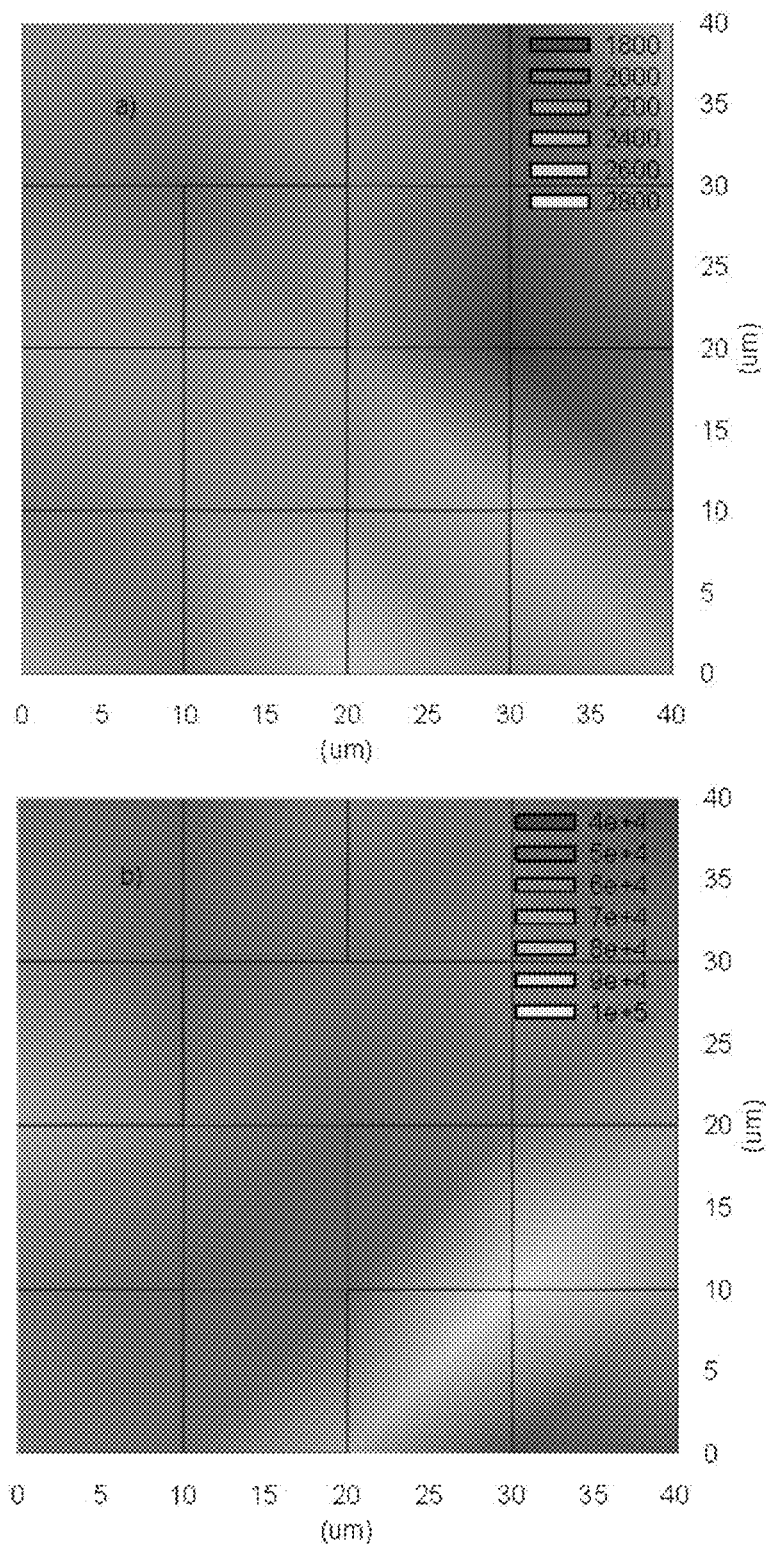
FIG. 3 shows Raman intensity images of homogeneity measurement for 600 Å thick SERS substrate a) gold film b) silver film. Scale from black to white indicates the relative SERS intensity.

SERS Measurements:

A Renishaw inVia microRaman instrument was used for studying the SERS substrate. The instrument consists a of 35 mW HeNe laser (632.8 nm) as the source, a motorized microscope stage sample holder and a CCD detector. The motorized microscope stage allows SERS maps of the surface to be formed. The instrument parameters were 50× objective and 10 second acquisition time. In addition, a fixed silicon wafer was used as a reference for normalizing the variation of power in different scans. To test the stability and photometric reproducibility of the instrument setup the uniformity of the silicon phonon peak was measured across a 40 μm$^2$ area of a highly uniform single crystal silicon substrate. The measurements show a ~4-5% spot-to-spot reproducibility due to fluctuations of the instrument optics, electronics and laser power. An area map was selected for uniformity calculations with 10% laser power (see FIG. 3).

Figure 4:
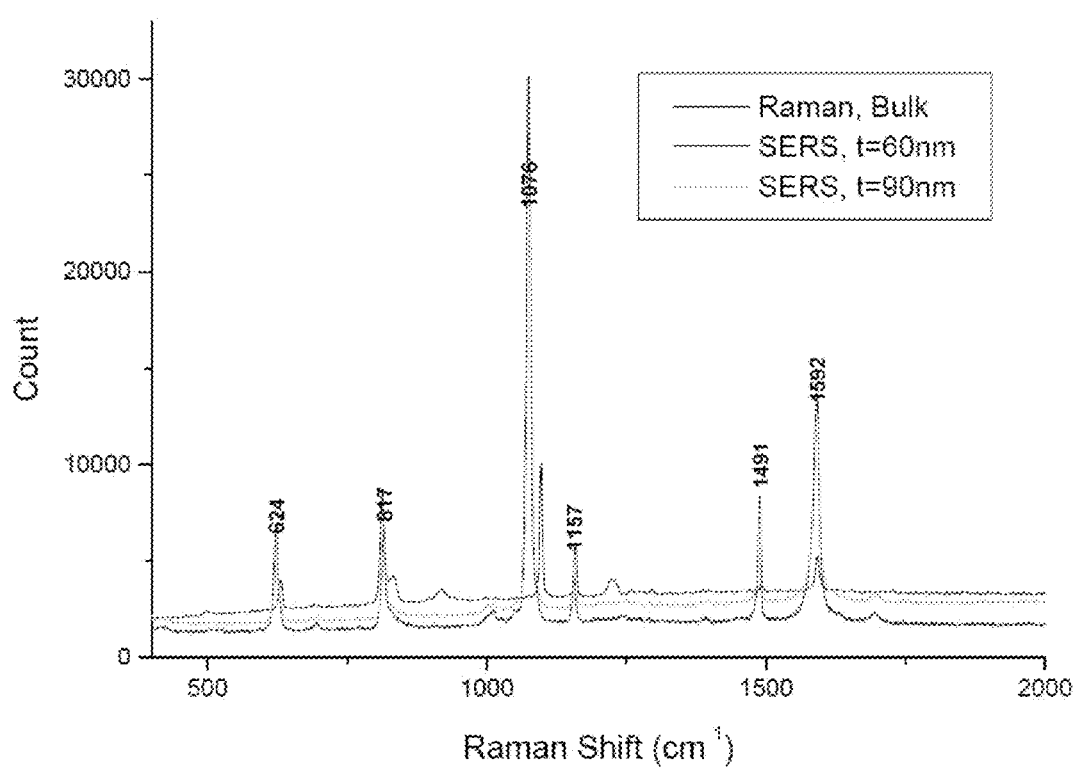
FIG. 4 shows Raman spectra of FBT and SERS spectra of FBT for 60 and 90 nm silver films.
Figure 5:
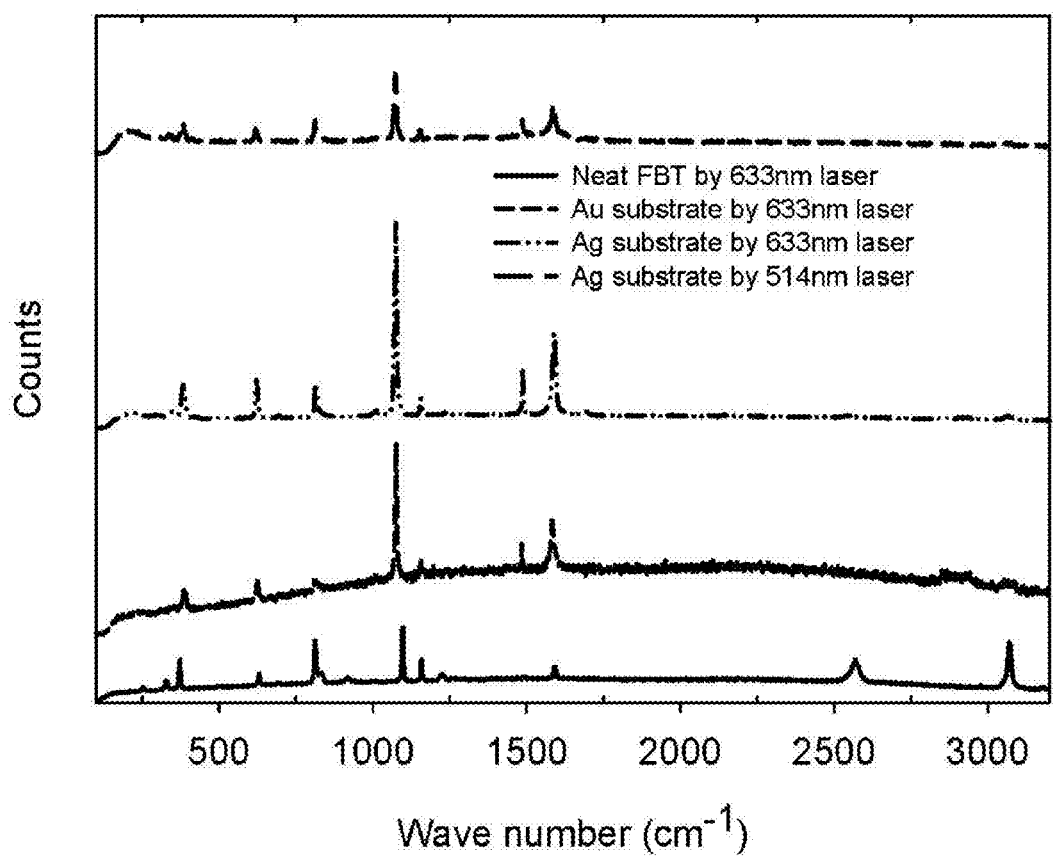
FIG. 5 shows Raman spectra for FBT on Ag and Au substrates and their dependence on laser wavelength.

To test the uniformity, enhancement factors (EFs) and reproducibility of the SERS signals, 4-fluorobenzenethiol (FBT) molecules were adsorbed onto the gold and silver substrates. First, the FBT C-F stretching mode signals were used for evaluating the effects of the metal layer thickness. FIG. 4 shows the data for 60 and 90 nm thick silver films. In general, the peak locations for all SERS measurements are consistent with the unenhanced Raman spectra. However, the spectra show a slight shift at 1076 cm$^{-1}$ peak for the SERS measurements. Gold films show similar effects but with the expected ~100× lower intensities (see FIG. 5). Second, the C-F stretch mode intensity is used for quantitative estimates of the EFs using the equation, $$EF(1077 \text{ cm}^{-1}) = \frac{N_{bulk} I_{poly}}{N_{poly} I_{bulk}} \quad (1)$$

where $I_{bulk}$ and $I_{poly}$ are the measured intensities of pure bulk FBT and the adsorbed molecules on the metal-coated polymer substrates and $N_{bulk}$ and $N_{poly}$ are the volume number density of bulk and adsorbed molecules, respectively. The resultant EFs for gold and silver were $10^4$ and $10^6$, respectively. The 521 cm$^{-1}$ peak of a silicon wafer was used as a reference for normalization of the spectra. The Raman C-F stretching intensity was determined by probing FBT on the Teflon using the Renishaw microRaman instrument. According to Renishaw, using the 50× objective, a probe volume of 0.8 fL was estimated by:

$$\tau_1 = 3.21\lambda^3 \left(\frac{f}{D_1}\right)^4 \quad (2)$$

In Eq. (2), λ is the laser wavelength (632.8 nm), f is the focal length of the objective (4 mm) and $D_1$ is the effective laser beam diameter at the back aperture of the objective (~4 mm). Given the density of FBT as 1.197 g/cm$^3$, the number of molecules contributing to SERS signal ($N_{bulk}$) is estimated as 4.6×10$^9$. The 50× objective with a numerical aperture of 0.75 gives a spot size of 514.7 nm for a 632.8 nm laser using the relation:

$$d_1 = \frac{0.61\lambda}{N \cdot A} \quad (3)$$

This value is the minimum laser focus under ideal conditions. However, experimentally, distortion of the laser by the holographic notch filter leads to broadening of the beam focus from 514.7 nm to around 1 μm. The number of molecules ($N_{poly}$) in the 1 μm diameter laser spot was determined as 3.6×10$^6$ assuming a planar gold surface. In reality, the actual surface area of laser spot is larger than planar gold surface.

The enhancing effect of the Raman spectra are generally attributed to two mechanisms: electromagnetic and chemical (Kneipp et al., "Surface-enhanced Raman scattering and biophysics" *J. Physics—Condensed Matter*, 14(18), R597-R624 (2002)). The former arises from the nanoscale scale roughness of the underlying PPX film which promotes excitations of localized surface plasmon resonances with amplified local electromagnetic fields. Chemical enhancement arises from coupling of the electronic polarizability of the molecule and underlying metal conduction electrons.

Bacterial Strains and Growth Conditions:

*E. coli* was purchased from Lucigen (BL21-DE3) and after subculturing, single colonies were collected using sterile plastic inoculating loops and cultivated for 4 h at 37° C. on a LB agar base. 10 μl of bacteria aliquots were placed on a SERS substrate for immediate characterization. *B. cereus* (ATCC #9818) was kindly provided by Dr. Stephanie Doores. After subculturing, single colonies were collected using sterile plastic inoculating loops and cultivated for 4 h at 37° C. on a LB agar base. Ten bacteria aliquots were placed on a SERS substrate for immediate characterization. Respiratory Syncytial Virus (RSV) was produced in Hep-2 cells grown in Opti-MEM (Invitrogen) with 2% fetal bovine serum (FBS), 1% L-glutamine, 50 U/mL penicillin and 50 μg/mL streptomycin. Five days after inoculation, virus-containing supernatant was harvested and clarified at 3200 g for 20 minutes. The virus was not recovered by lysing cells to minimize contamination of particles by host nucleic acid, which is visible on the surface of particles purified by cell lysis by SERS. Supernatant was brought to 50 mM Tris, pH 7.5, 0.1 M MgSO$_4$ and precipitated at 4° C. for 90 min with moderate stirring using a final concentration of 10% PEG 6000. The precipitate, containing viral particles, was collected by centrifugation at 3200×g for 20 minutes. The pellet was gently resuspended in 7 mL of cold buffer consisting of 150 mM NaCl, 50 mM Tris-HCl, 100 mM MgSO$_4$ and layered onto a discontinuous (30%, 45%, 60%) sucrose gradient. Samples were centrifuged in a Beckman SW28 rotor at 100,000×g at 4° C. for 100 minutes. The 2-3 mL interface between the 30% and 45% sucrose layers was collected and 1 mL aliquots were frozen for titer and subsequent use. Infectious titer was determined by plaque assay on Hep-2 cells and total virus titer was determined by quantitative PCR. Coxsackievirus B3 strain (ATCC VR30) was kindly provided by Dr. Craig Cameron and was used as received.

Gram-positive and gram-negative bacteria were selected as test organisms for pathogen detection. Diluted bacterial samples were analyzed on the SERS substrate (~10$^4$ cells in 1 mm$^2$ area). The results definitively show detection with clear differentiation between the two species. The differentiation is related to the different cell wall structures; both organisms possess a peptidoglycan layer but gram-negative organisms have an additional structure of lipopolysaccharides (LPS).

Figure 6:
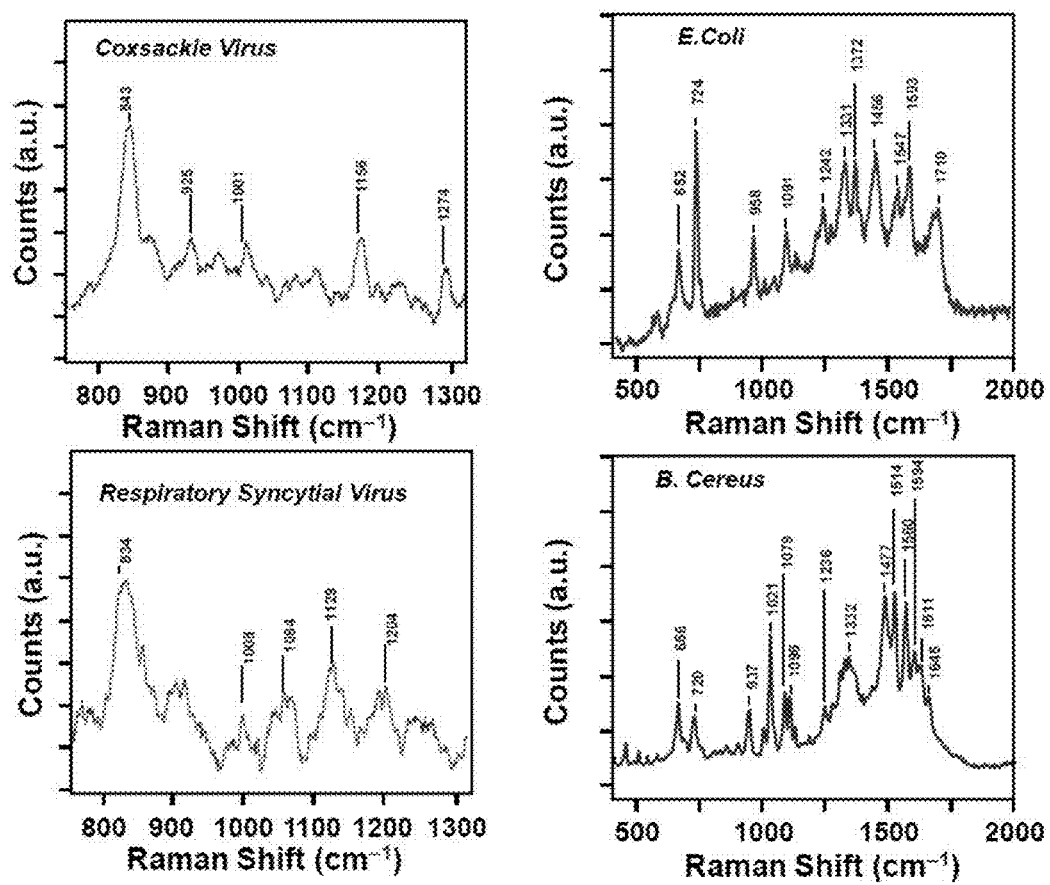
FIG. 6 shows SERS spectra of single entities of Coxsackievirus (non-enveloped virus), Respiratory Syncytial Virus (enveloped virus), *E. coli* (Gram-negative bacteria), and *B. cereus* (Gram-positive bacteria) adsorbed onto 60 nm Ag metallized PPX-Cl substrates.

FIG. 6 shows the SERS spectra of single *E. coli, B. cereus*, Coxsackie, and RSV pathogen particles on the nanostructured silver substrates. Spectra were collected at 2.5 mW laser power, 632 nm wavelength and a 10 s collection time.

Figure 7:
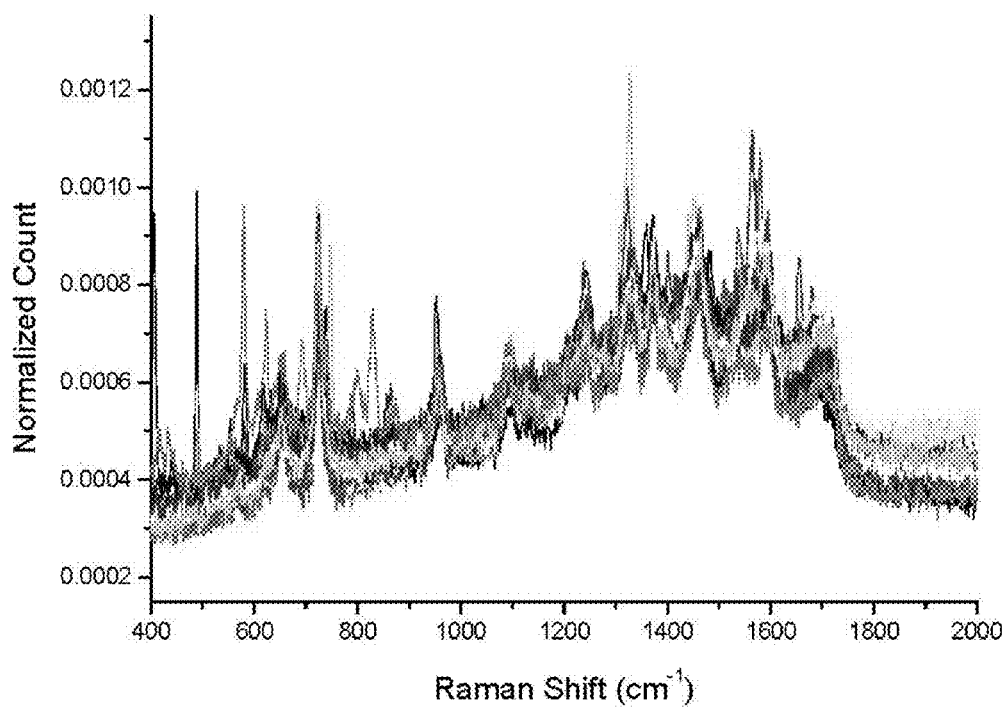
FIG. 7 shows *E. coli* SERS spectra collected from 25 individual cells.

Typical Raman bands of membrane proteins, phospholipids (C-C stretching (Susi et al., "Laser-Raman Investigation of Phospholipid-Polypeptide Interactions in Model Membranes" *Biochemistry*, 18(2), 297-301 (1979))) and polysaccharides (Jarvis et al., "Discrimination of bacteria using surface-enhanced Raman spectroscopy" *Analytical Chemistry*, 76(1), 40-47 (2004)) can be observed on the spectra. The SERS spectra match well with the literature (Premasiri et al., "Characterization of the Surface Enhanced Raman Scattering (SERS) of bacteria" *J. Physical Chemistry B*, 109(1), 312-320 (2005)) and the peak positions are listed in Table 1. The peak assignments for *E. coli* and *B. cereus* are very similar, however, the intensities of the spectra vary drastically which is the key for differentiating these two test organisms. SERS spectra on silver substrates were highly reproducible for the two bacteria. From spot to spot (i.e., individual cells), the variation of peak intensity signal at 1372 cm$^{-1}$ is calculated as 15% for the *E. coli* data (see FIG. 7).

TABLE 1

SERS Spectral Peaks for Bacteria Adsorbed onto Hybrid Metal-Organic nanostructured Thin Films

| | SERS shift (cm$^{-1}$) | | | |
|---|---|---|---|---|
| assignment | E. coli | B. cereus | RSV | Coxsackie-virus |
| guanine, tyrosine (nucleic acid) | 653 | 656 | | 686 |
| adenine | 724 | 720 | | 724 |
| tyrosine | | | 837 | 842 |
| C═C deformation | 958 | 937 | | 925 |
| phenylalanine | | | 1004 | 1002 |
| C—C stretching (phospholipids or carbohydrates) | | 1022 | | |
| C—N stretching (glycoprotein) | | | 1064 | |
| carbohydrates (C—C stretching, C—O—C stretching) | | | | |
| C—C stretching (protein) | | | 1130 | 1156 |
| tyrosine | | | 1204 | |
| thymine | | | | 1272 |
| O—P—O— symmetric stretching (DNA) | 1091 | 1096 | | |
| amide III (random) | 1242 | 1236 | | |
| adenine, guanine (protein), CH deformation | 1330 | 1332 | | |
| COO— stretching | 1372 | | 1320 | 1337 |
| CH2 deformation | 1456 | 1477 | 1480 | 1437 |
| amide II | | 1559 | | |
| adenine, guanine (ring stretching) | 1593 | 1594 | 1610 | 1603 |
| amide I | 1710 | 1650 | | |

The spectra reveal that the bio-organisms were captured as an integral species with no significant degradation, as shown by reasonable assignments of the vibrational features based on standard empirical peak correlations. Typical Raman bands of proteins, phospholipids, and polysaccharides can be observed in the *E. coli* and *B. cereus* bacteria spectra (Table 1) and spectra match well with the literature (Premasiri et al., *Journal of Physical Chemistry B*, 109, 312 (2005); Jarvis et al., *Analytical Chemistry*, 76, 40 (2004); Schuster et al., *Analytical Chemistry*, 72, 5529 (2000)). The band at 653 cm$^{-1}$ is most likely from guanine and tyrosine. The strong band at 724 cm$^{-1}$ is likely from polysaccharides and adenine while that 958 cm$^{-1}$ is likely from C═C deformation. The band at 1091 cm$^{-1}$ correlates with those expected from carbohydrates (mainly from C—C stretching, C—O—C stretching of 1,4-glycosidic link may also contribute to the peaks). For *E. coli*, the peak at 1710 cm$^{-1}$ can be associated with the C═O of an ester group. The amide I (C═O stretching and C—N—H deformation) bands, which are the characterizations of protein backbones, can be assigned to peaks in the vicinity of 1650 and 1240 cm$^{-1}$, respectively. The band at 1372 cm$^{-1}$ is most likely from COO— stretching. The band at 1456 cm$^{-1}$ is expected for CH$_2$ deformation. The band at 1593 cm$^{-1}$ correlates with adenine and guanine (ring stretching). For RSV, the SERS bands at ~830 and 1005 cm$^{-1}$ are presumed to be from tyrosine and phenylalanine, respectively (Bao et al., *Journal of Roman Spectroscopy*, 32, 227 (2001)), while those at ~1060 and ~1130 cm$^{-1}$ can be ascribed to C—N stretching and C—C stretching, respectively (Shanmukh et al., *Nano Letters*, 6, 2630 (2006)). Tyrosine is also supposed to show Raman features at ~1200 cm$^{-1}$. For Coxsackievirus, the SERS band at 688 cm$^{-1}$ is assigned to guanine and tyrosine. Other major SERS bands present at 724, 843, 925, 1001, 1156 and 1274 cm$^{-1}$, are most likely from adenine, tyrosine, C═C deformation, phenylalanine, C—C stretching (protein) and thymine, respectively. In all cases the peaks fit with expected features for the organisms. Further work is needed in order to find deeper correlations with the exact details of the attachment point of the organism on the SERS surface and the appearance of various constituent groups located in different regions of the organism.

Figure 8:
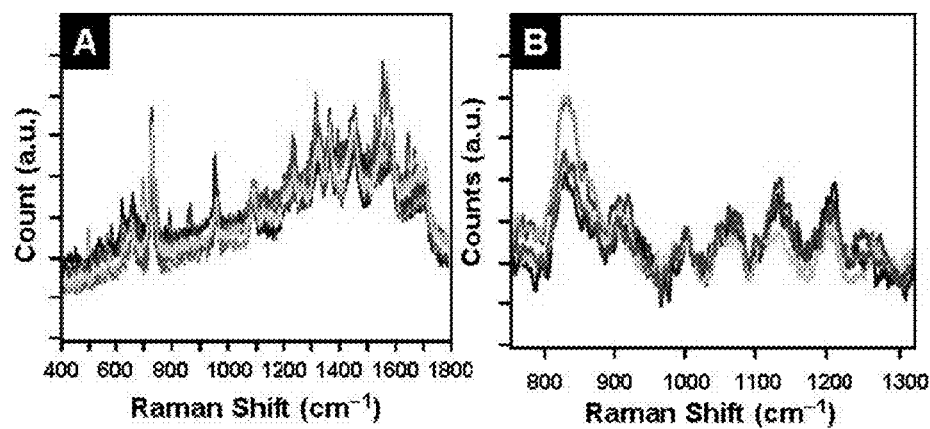
FIG. 8 shows sets of superimposed (a) *E. coli* and (b) RSV SERS spectra collected from nanostructured PPX films coated with a thin 60 nm Ag layer. The variation of the *E. coli* spectra on the silver SERS substrate was obtained from 20 individual cells. The peak at the 1372 $cm^{-1}$ shows a relative deviation of 15%. The variation of the RSV spectra on the silver SERS substrate was obtained from 6 individual particles.

FIGS. 8(*a*) and (*b*) show the reproducibility of SERS spectra of single *E. coli* and RSV pathogen particles on the nanostructured silver substrates, respectively. Both data were collected at 2.5 mW laser power and 632 nm wavelength with a 10 s collection time. The *E. coli* data were collected by first identifying the location of a bacteria particle (~1 μm size) by optical microscope imaging on the substrate with the images taken randomly with wide distances between (>>1 ∞m) bacterial particle. The RSV data were collected using an automated surface scan to statistically find a particle within the image field since the pathogens were of too small a size to readily identify their location. Again, wide variations in the sampling distances were used. The data show highly reproducible spectra across a surface with a relative deviation of 15% for the *E. coli* spectra with 20 samples; the RSV spectra were similarly reproducible, though only 6 particles were analyzed. Preliminary data show that the high reproducibility is also maintained from substrate to substrate with careful control of preparation and bio-organism capture.

In order to check the reproducibility of the Ag/PPX-Cl films relative to standard Ag island films on glass, samples of the latter substrates were prepared with identical vapor deposition of Ag films on clean glass slide substrates and *E. coli* bacteria were collected on the substrates using the identical procedures as for the Ag/PPX-Cl substrates. After many trials, it was clear that while excellent EFs were obtained, the Ag islands were highly unstable in an unpredictable way to the collection process. This led to irreproducible SERS spectra for the bacteria particles across the surfaces, often with well over orders of magnitude variations in the signal intensities and with significant shifts in the relative fingerprint peak intensities.

Example 2

Materials:

All chemicals were A.C.S reagent grade and were used as received. Deionized water of 18.1 MΩ·cm was used for all experiments using a Barnstead Nanopure Diamond™ dispenser. Dichloro-[2,2]paracyclophane, the precursor for PPX deposition was purchased from Parylene Distribution Services Inc. p-type Si(100) were purchased from Wafernet Inc. San Jose, Calif. and were used as substrates for OAP-PPX deposition. A proprietary electroless catalyst kit purchased from Rohm and Haas (Shipley Co.) was used, consisting of CATAPREP™ 404 (stabilizer), CATAPOSIT™ 44 (Pd/Sn concentrate), and Accelerator 19™ (reaction accelerator). Fidelity™ 1026A and B electroless copper bath was purchased from OMG Fidelity Inc and used according to the manufacturer's directions.

OAP-PPX:

Si(100) (Wafernet Inc., CA) wafers were used as the substrate to deposit the OAP-PPX films. For good adhesion of the hydrophobic PPX films to the silicon surface, a self assembled monolayer (SAM) of allyltrimethoxysilane (Gelest Inc., PA) was deposited on the silicon surface. For the SAM deposition, a fresh silicon wafer was cleaned with a 1/1 (v/v) solution of HCl (36.5-38% w/w) and methanol (98.5% w/w) for 30 min. Afterwards, the wafer was rinsed in DI water and dried under N$_2$ gas. It was then kept in concentrated H$_2$SO$_4$ (95-98% w/w) for another 30 min. The wafer was then rinsed thoroughly in DI water and dried under N$_2$ gas. This treatment converted the siloxane groups of the native oxide silicon surface to silanol groups that can then bind the allyltrimethoxysilane molecules. 1% (v/v) allyltrimethoxysilane (Gelest, PA) in toluene containing 0.1% (v/v) acetic acid was used as the SAM solution. The wafer was treated in the SAM solution for 60 min under ambient temperature and dried on a hot plate at 140° C. for 5 min to remove the solvent molecules. The wafer was stored in a dark container at a temperature of 4° C. until required for the polymer deposition.

For OAP-PPX deposition, the method employed by Gorham involving deposition of PPX films using a low pressure, vapor deposition technique was modified (Gorham, "A New General Synthetic Method for Preparation of Linear Poly-P-Xylylenes" *Journal of Polymer Science Part A-1—Polymer Chemistry*, 4, 3027 (1966)). Poly(chloro-p-xylylene) (PPX-Cl), a halogen derivative of poly(p-xylylene) (PPX), was chosen for all experiments. Dichloro-[2.2]paracyclophane (PDS Inc., TX) was used as the precursor for the deposition. The precursor was sublimed at a temperature of 175° C. under a pressure of ~10 torr. The precursor vapor was then pyrolyzed at 690° C. The pyrolysis of dichloro[2.2]paracyclophane resulted in the cleavage of the alkyl bridge to form free-radicals. The free-radicals were directed at an angle of <10° on the silicon substrate using a tilt-nozzle. The resulting film was a low-density porous polymer with unique nanostructured morphology.

Electroless Metal Plating:

Three variations were developed for coating the OAP-PPX film with metal to produce SERS-active composite substrates. These include two direct electroless processes and a galvanic exchange process, which can be employed with certain metal films deposited onto the OAP-PPX film via either electroless method or the vapor deposition metallization procedure described in Example 1. The two direct electroless metal deposition methods include the use of a conventional colloidal Pd/Sn electroless catalyst to directly catalyze the PPX surface for plating and the use of a Sn-free Pd(II) colloid as an electroless catalyst covalently binding to a ligand physisorbed to the OAP-PPX film.

The direct electroless plating process involving Pd/Sn is illustrated by the plating of electroless Cu onto the PPX-Cl film. For the electroless copper plating of OAP-PPX films the following solution were prepared and used as required.

1. Pd/Sn Catalyst:
Pd/Sn catalyst was freshly prepared just before use. To prepare the Pd/Sn catalyst, 10 g of CATAPREP™ 404 stabilizer (Shipley Inc.) was weighed and dissolved in ~45 mL of $H_2O$. This solution was transferred to a 50 mL volumetric flask. 1.5 mL of CATAPOSIT™ 44 Pd/Sn concentrate (Shipley Inc.) was then added using a micropipette and diluted to the mark using $H_2O$. The flask was tightly sealed because the colloid is $O_2$ sensitive if exposed for extended times. It is advisable to flush the flask above the colloid with argon before sealing the flask.

2. Accelerator:
10 mL of Accelerator 19™ (Shipley Inc.) was dissolved in 100 mL of $H_2O$ in a volumetric flask. The flask was sealed until the solution was used.

3. Electroless Copper Bath:
Copper baths were freshly prepared before each experiment. To prepare a stock solution, 5 mL of Fidelity 1026A and 5 mL of Fidelity 1026B solution were added to a 50 mL volumetric flask. $H_2O$ was added to dilute the solution up to the mark. 25 mL of this stock solution was dissolved in 75 mL of $H_2O$. The resultant 25% electroless copper bath was used to plate polymer surfaces with copper. Other baths were prepared with different strengths by varying the dilution.

The efficacy of the Pd/Sn catalyst and the electroless copper bath were tested by plating polystyrene (PS) weighing boats. The PS weighing boats were treated with Pd/Sn catalyst for 5-10 min. The excess catalyst was carefully removed from the surface via a Pasteur pipette and discarded. After the treatment of PS with the Pd/Sn catalyst the treated area could be wetted. The PS surface was then gently rinsed in 0.12 M HCl (aq) solution for 5-10 s. Care was taken not to pour the HCl solution directly on the PS as it can remove some of the bound Pd/Sn catalyst. Immediately after HCl treatment, the PS was immersed in the accelerator solution for 30 s. The PS was immediately rinsed with $H_2O$ and transferred to the electroless copper bath solution of 10-25% strengths as per the experiments. The plating was allowed to continue for 10-15 min. The copper plated PS weighing boats were rinsed twice in $H_2O$ and dried under $N_2$ gas.

For OAP-PPX, the films were treated with the Pd/Sn catalyst solution for 10 min. However, unlike PS, the OAP-PPX films did not show any visible wetting of the catalyst treated surface. The films were then treated with HCl and accelerator solution and rinsed with $H_2O$ as explained previously for PS plating. For copper plating, the Fidelity electroless Cu bath was diluted to 25% strength with water (1 volume Cu bath/3 volumes water) and the plating was carried out at 22±1° C. for a desired time ranging from 3-10 min. At the conclusion of the electroless plating, the films were rinsed twice in $H_2O$ and dried under $N_2$ gas until needed for further experiments or SERS studies.

Galvanic Ag Plating:

The galvanic plating process is illustrated using the freshly prepared electroless Cu films prepared by the direct Pd/Sn electroless procedure described above. For galvanic silver plating, copper plated OAP-PPX films were immersed in freshly prepared $AgNO_3$ (0.5 g of $AgNO_3$ dissolved in 20 mL of $H_2O$) solution. The reaction was allowed to continue for 60 s during which the solution was gently agitated. The films were rinsed twice in $H_2O$ and dried under $N_2$ gas.

Figure 9:
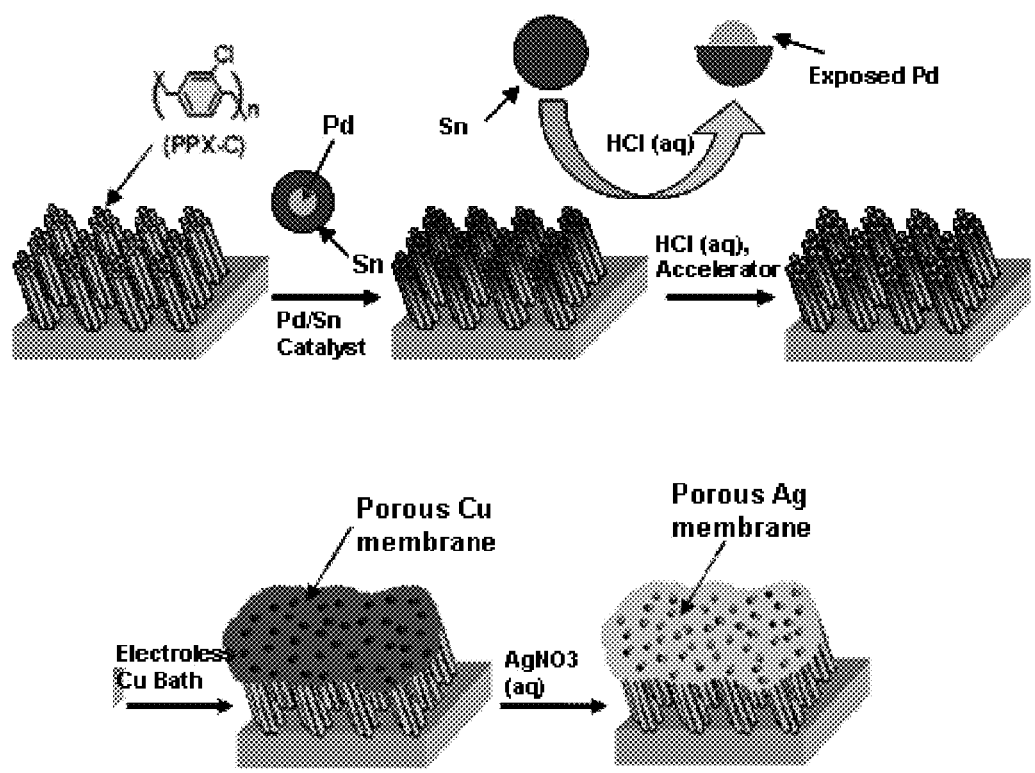
FIG. 9 shows a schematic description of the galvanic route for Ag metallized SERS substrate preparation.

Galvanic exchange can be used to deposit metal films by displacing another metal that is lower in the galvanic series. FIG. 9 shows the scheme that was used to deposit a Ag membrane by galvanic exchange on a Cu membrane. Cu membranes were prepared by electroless deposition on PPX-Cl film using a commercially available Pd—Sn catalyst and copper bath. Copper was displaced on the surface by a simple immersion of the films in $AgNO_3$ for a few minutes. Due to the higher standard reduction potential of Ag compared to Cu, Ag reduction on Cu is thermodynamically feasible:

$$Ag^+ + e^- \leftrightarrows Ag_{(s)}, E°=0.799 \text{ V}$$

$$Cu^+ + e^- \leftrightarrows Cu_{(s)}, E°=0.52 \text{ V}$$

$$Cu^{2+} + 2e^- \leftrightarrows Cu_{(s)}, E°=0.34 \text{ V}$$

Therefore, when $AgNO_3$ is treated with a Cu film spontaneous reaction takes place at the interface where Ag is deposited.

Electroless Ag Plating:

The second direct electroless method involving covalently binding a Sn-free colloidal Pd(II) catalyst to a ligand physisorbed onto the OAP-PPX film is illustrated via the fabrication of an electroless silver-OAP-PPX composite. Electroless silver can be deposited directly on the OAP-PPX films using a non-covalent ligand binding method (Demirel et al., "A Non-Covalent Method for Depositing Nanoporous Metals via Spatially Organized Poly (P-xylylene) Films" *Advanced Materials*, 19, 4495-4499 (2007)). Briefly, OAP-PPX films were incubated in 1 M pyridine (aq) solution for 48 hours.

Pyridine molecules enter the polymer network and are stabilized by the π-π interaction with the aromatic polymer chain. Films are then treated with a palladium based colloidal $Pd^{II}$ dispersion, Pd1 for 45 min. The details of the preparation of Pd1 are explained elsewhere (Dressick et al., "Characterization of a Colloidal Pd(II)-based Catalyst Dispersion for Electroless Metallization" *Colloids & Surfaces A,* 108, 101-111 (1996)). The films were then placed in the electroless silver bath for 6 h. The composition of the electroless silver bath is $AgNO_3$ (0.05 M), $(NH_4)_2SO_4$ (0.9 M), $NH_3$ (2.1 M), $CoSO_4.7H_2O$ (0.12 M), pH=10.

Figure 10:
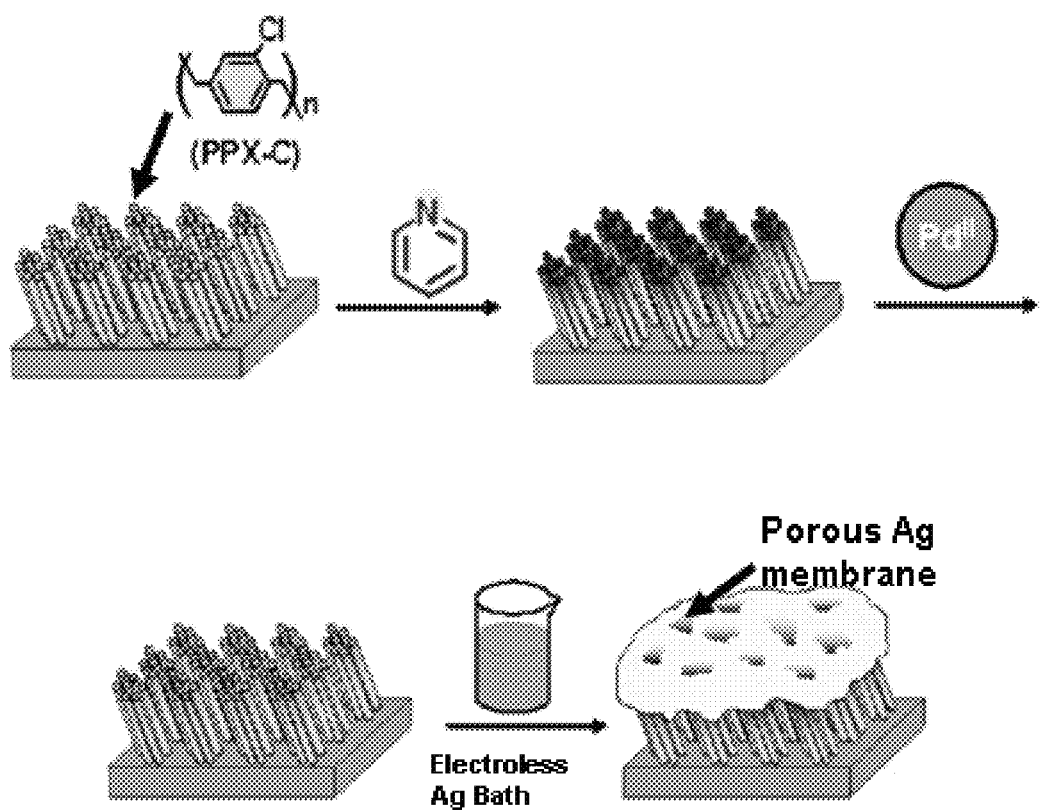
FIG. 10 shows a schematic description of the non-covalent route for Ag metallized SERS substrate preparation.

FIG. 10 depicts the scheme used to deposit Ag nanoparticles on the PPX-Cl films using a non-covalent ligand physisorption route. The highly open and amorphous nature of the oblique angle polymerized PPX-Cl (OAP-PPX) film allows it to physisorb ligand molecules such as pyridine. The adsorbed pyridine molecules are stabilized by π-π and/or van der Waals interactions with the aromatic PPX-Cl backbone. It should be noted that although the binding is based on the weak non-covalent interaction, an array of such interactions can produce enough attraction to stabilizing metal nanoparticles. Pyridine treated OAP-PPX-Cl films are then transferred to the Pd1 dispersion. Covalent binding between the $Pd^{II}$ colloid and the N-sites of the pyridine molecules occur. PPX-Cl films are then transferred to the electroless Ag bath after activation in $AgNO_3$ solution. The Pd(0) and Ag(0) produced by reduction of the $Pd^{II}$ and $Ag^+$ by the reducing agent of the electroless Ag bath act as the catalytic sites for the nucleation and growth of Ag nanoparticles. If the films are kept in the Ag bath for a longer time the Ag nanoparticles grow to form a continuous porous film on the PPX-Cl surface. In addition to the non-covalent interactions, metal adhesion is further improved by the anchoring effect due to the nanostructured morphology.

Characterization:

The nanostructured surface morphology was characterized by an atomic force microscope (Nanoscope E, Veeco) using silicon nitride cantilevers (Veeco Metrology, CA) in contact mode. RMS roughness data was recorded for three 5 μm×5 μm random scans on each sample. Field-emission Scanning electron microscope images of the film surface were taken using a FE-SEM (JEOL 6700F, Japan) operated at 3 KV accelerating voltage.

SERS Measurements:

4-fluorothiophenol (FBT) (Caution: Stench from FBT. Use only in a well-ventilated fume hood) was used as the analyte to measure the SERS enhancement and signal uniformity of the metal/OAP-PPX composite substrates prepared by each of the three solution-based metallization methods described above in this example. The analyte solution was prepared by dissolving 20 μL of FBT in 20 mL of ethyl alcohol. Silver or copper plated OAP-PPX films were immersed in the FBT solution and stored overnight in a sealed vial. Afterwards, the films were removed and rinsed in ethyl alcohol for 1 min to remove any physisorbed FBT molecules. The films were then immediately characterized for SERS enhancement.

A Renishaw inVia microRaman with a 35 mW HeNe laser (λ=632.8 nm) was used to study the SERS substrate. For each sample the 50× objective lens and 10 s acquisition time was used. The acquisition power was varied as required for each sample. For the normalization of the SERS spectra due to the variation in the acquisition power, a Raman spectrum of Si(100) was used as the reference. For spectrum uniformity calculation, SERS spectra of 25 randomly selected spots over an area of 1 $mm^2$ with 10% laser power were used.

Figure 11:
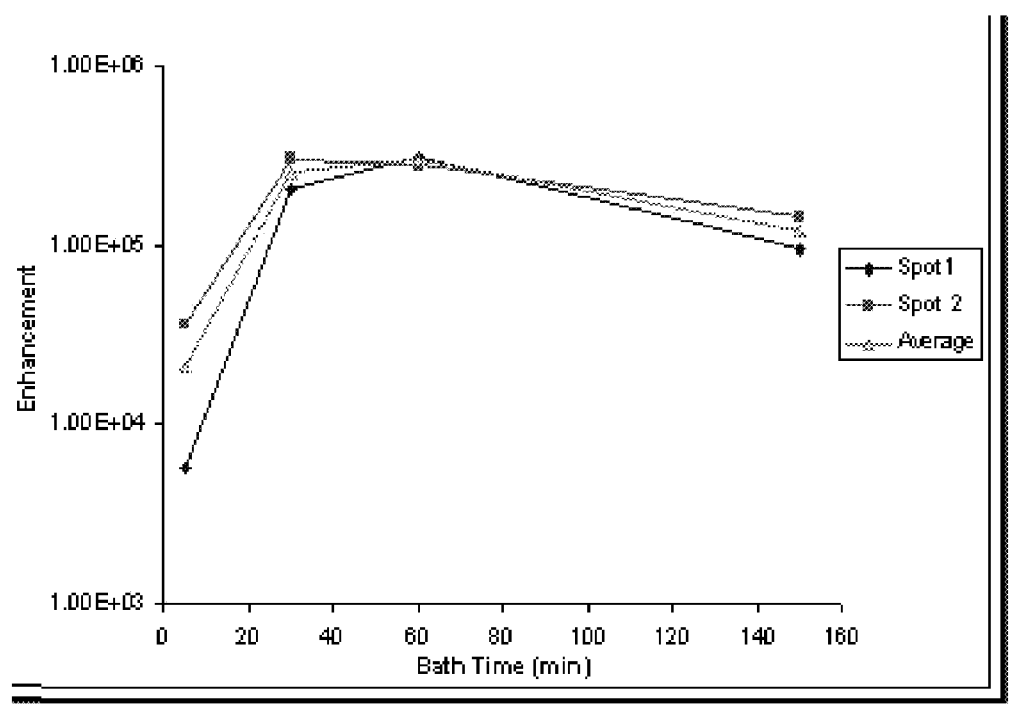
FIG. 11 shows the enhancement factor (EF) with regard to bath time for the non-covalent route.

FIG. 11 shows the SERS enhancement factor obtained from the 1077 $cm^{-1}$ (Eq. (1)) peak of bound FBT molecules as a function of treatment time in the electroless Ag bath for an electroless silver/OAP-PPX composite substrate. The substrate was prepared by the route of FIG. 10 involving initial physisorption of pyridine onto the OAP-PPX substrate, followed by covalent binding of the Sn-free colloidal Pd(II) catalyst to the pyridine and electroless Ag deposition onto the catalytic Pd sites. At lower bath time in FIG. 11, the Ag particle-particle separation is too large for any "hot spots" formation on the surface and the enhancement factor is low. On the other hand, at long bath times, the Ag nanoparticles grow and fuse together to form a continuous film. The smoother Ag film formed by fusion of the Ag nanoparticles again limits the magnitude of the enhancement factor. At intermediate times, a situation occurs in which Ag nanoparticle size and distribution on the nanostructured OAP-PPX surface are optimal and a maximum enhancement factor of ~3×10$^5$ is obtained. This occurs at ~30 min of Ag electroless bath time in FIG. 11 for the metal film deposited via the non-covalent ligand physisorption route.

Figure 12:
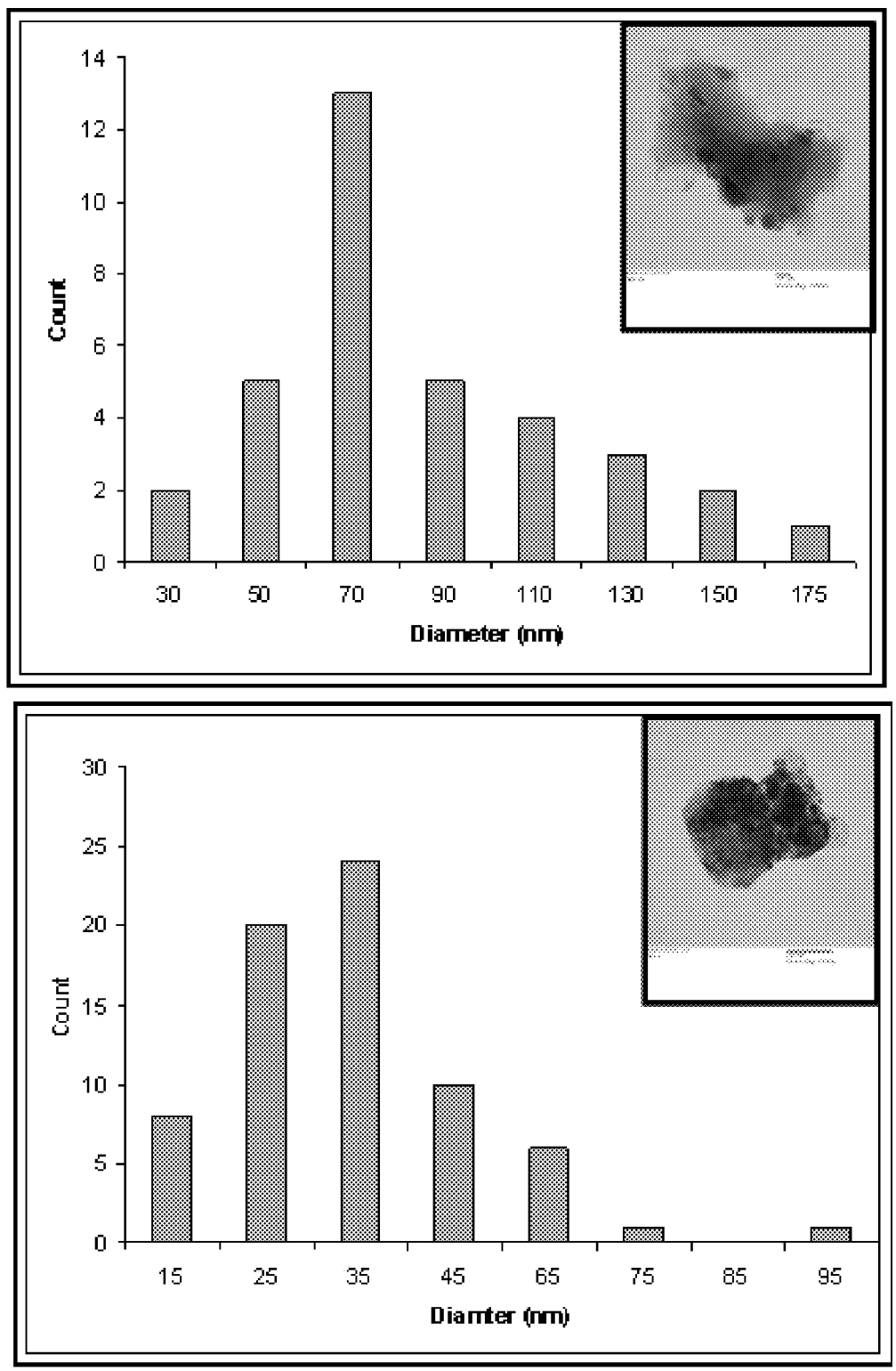
FIG. 12 shows the size distribution for columnar nano-PPX films using the non-covalent route (top) and the galvanic route (bottom). Insets show TEM images of the Ag nanoparticles. Both measurements are carried out for the sample with highest SERS enhancement in FIG. 11.

A typical size distribution of the Ag nanoparticle features is given in FIGS. 12(*a*) and (*b*) for the examples of Ag film deposited on a PPX-Cl substrate using non-covalent ligand physisorption route and galvanic route, respectively. The figures show histograms, constructed from several cross section transmission electron microscope (TEM) images, with an average Ag particle diameter of ~70 nm and ~35 nm respectively. The insets in FIG. 12 show examples of a TEM image of the nanoparticles. FIG. 12 illustrates the ability to control Ag film morphology via the metallization method selected for fabrication of the composite. This, in turn, allows control of SERS activity. For example, the ~70 nm Ag nanoparticles of FIG. 12(*a*), formed via the non-covalent ligand physisorption electroless process, exhibit a SERS enhancement factor of ~3×10$^5$. In contrast, the ~35 nm Ag nanoparticles formed via galvanic exchange of the electroless Cu films prepared on identically structured OAP-PPX substrates via electroless Cu plating of Pd/Sn catalyzed OAP-PPX exhibit a different SERS enhancement factor. Specifically, a Pd/Sn catalyzed OAP-PPX substrate treated 10 min by the electroless Cu bath, followed by 60 s galvanic exchange with $AgNO_3$ to form the Ag exterior film as described above, exhibits a SERS enhancement factor of ~3×10$^5$. Consequently, through a simple change in the method for deposition of the metal film the SERS enhancement factor can be tuned by a factor of 10.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A structure comprising:
   a substrate;
   a spatially organized polymer nanostructured thin film on the substrate;
     wherein the film comprises one more assemblies of parallel nanowires or submicron wires inclined at an angle other than a right angle with respect to the substrate; and
   a metal coating on the thin film;
     wherein each nanowire or submicron wire is fully encapsulated by the metal coating;
     wherein the thin film is made by a method comprising:
       directing a pyrolyzed monomer vapor towards the substrate at an angle other than perpendicular to the substrate; and polymerizing the monomer or pyrolyzed monomer on the substrate;
wherein the metal coating is deposited on the thin film on a surface of the thin film opposed to the substrate;
wherein the monomer is one or more of a [2.2]-cyclophane, dichloro-[2.2]-cyclophane, an amino-[2.2]-cyclophane, a diamino-[2.2]-cyclophane, an aminomethyl-[2.2]-cyclophane, a trifluoroacetyl-[2.2]-cyclophane, and dibromo-[2.2]-cyclophane; and
wherein the monomer is vapor-phase pyrolyzed to form a poly-p-xylylene on the substrate.

2. The structure of claim 1, wherein the metal coating comprises a surface enhanced Raman spectroscopy-active metal or a surface enhanced resonance Raman spectroscopy-active metal.

3. The structure of claim 1, wherein the metal coating comprises one or more of silver, gold, copper, nickel, and platinum.

4. The structure of claim 1, wherein the metal coating is deposited by thermal evaporation.

5. The structure of claim 1, wherein the metal coating is deposited by sputtering.

6. The structure of claim 1, wherein the metal coating is deposited by electroless deposition.

7. The structure of claim 1, wherein the metal coating is deposited by:
binding a colloidal Pd/Sn catalyst to the thin film;
removing a portion of the Sn by treating the bound catalyst with one or more of hydrochloric acid and fluoroboric acid; and
depositing one or more metal layers overlaying the Pd/Sn catalyst.

8. The structure of claim 7, wherein the metal layers are deposited by exposing the thin film bearing the Pd/Sn catalyst to an electroless silver, gold, copper, nickel, or platinum bath.

9. The structure of claim 1, further comprising:
treating the metal coating with a solution containing ions of a more noble metal than the metal of the metal coating, to induce at least partial dissolution of the metal coating with concurrent deposition of a thin layer of the more noble metal via a galvanic exchange process.

10. The structure of claim 9;
wherein the metal coating comprises copper, nickel, cobalt, or iron or alloys thereof; and
wherein the more noble metal comprises gold, platinum, or silver.

11. The structure of claim 1, further comprising:
a layer of one or more ferromagnetic metals by e-beam deposited on the metal coating.

12. The structure of claim 1, further comprising:
a layer of chromium or titanium between the polymer and the metal coating.

13. A method comprising:
exposing the structure of claim 1 to a sample suspected of containing an analyte; and
performing a surface enhanced Raman spectroscopy analysis or a surface enhanced resonance Raman spectroscopy analysis of the exposed structure.

14. The method of claim 13, wherein the analyte is a virus, bacterium, protozoan, or a cell from a multicellular or unicellular organism.

15. The method of claim 14, wherein the analyte is living.

16. The method of claim 13, wherein the analyte is an aerosol or dust particle.

17. The method of claim 13, wherein the analyte is a liquid or solution comprising organic or inorganic molecules, macromolecules derived from a biological source, engineered macromolecules derived from a chemical or biological source, proteins, antibodies, lipids, polysaccharides, nucleic acids, membranes, organelles of a cell, viruses, bacteria, protozoa, or cells from a multicellular or unicellular organism.

18. A method comprising:
providing a spatially organized polymer nanostructured thin film on a substrate;
wherein the film comprises one more assemblies of parallel nanowires or submicron wires inclined at an angle other than a right angle with respect to the substrate; and
depositing a metal coating on a surface of the thin film opposed to the substrate;
wherein each nanowire or submicron wire is fully encapsulated by the metal coating;
wherein the thin film is made by a method comprising:
directing a pyrolyzed monomer vapor towards the substrate at an angle other than perpendicular to the substrate; and
polymerizing the monomer or pyrolyzed monomer on the substrate;
wherein the monomer is one or more of a [2.2]-cyclophane, dichloro-[2.2]-cyclophane, an amino-[2.2]-cyclophane, a diamino-[2.2]-cyclophane, an aminomethyl-[2.2]-cyclophane, a trifluoroacetyl-[2.2]-cyclophane, and dibromo-[2.2]-cyclophane; and
wherein the monomer is vapor-phase pyrolyzed to form a poly-p-xylylene on the substrate.

19. The method of claim 18, wherein the metal coating is deposited by thermal evaporation.

20. The method of claim 18, wherein the metal coating is deposited by sputtering.

21. The method of claim 18, wherein the metal coating is deposited by electroless deposition.

22. The method of claim 18, wherein the metal coating is deposited by:
adsorbing a ligand adsorbate onto the thin film;
binding a Pd catalyst to the ligand adsorbate adsorbed onto the thin film;
depositing one or more metal layers or metal nanoparticles overlaying the Pd catalyst and ligand adsorbate.

23. The method of claim 22;
wherein the ligand adsorbate is adsorbed by exposing the thin film to a pyridine solution or vapor;
wherein the Pd catalyst is bound by exposing the thin film to a Pd catalyst; and
wherein the metal layers or metal nanoparticles are deposited by exposing the thin film to an electroless silver, gold, copper, nickel, or platinum bath.

24. The method of claim 18, wherein depositing one or more metal layers comprises:
binding a colloidal Pd/Sn catalyst to the thin film;
removing a portion of the Sn by treating the bound catalyst with one or more of hydrochloric acid and fluoroboric acid; and
depositing one or more metal layers overlaying the Pd/Sn catalyst.

25. The method of claim 24, wherein the metal layers are deposited by exposing the thin film bearing the Pd/Sn catalyst to an electroless silver, gold, copper, nickel, or platinum bath.

26. The method of claim 18, further comprising:
treating the metal coating with a solution containing ions of a more noble metal than the metal of the metal coating, to induce at least partial dissolution of the metal coating with concurrent deposition of a thin layer of the more noble metal via a galvanic exchange process.

27. The method of claim 26;
wherein the metal coating comprises copper, nickel, cobalt, or iron or alloys thereof; and
wherein the more noble metal comprises gold, platinum, or silver.

28. The method of claim 18, further comprising:
depositing a layer of one or more ferromagnetic metals by e-beam deposition on the metal coating.

29. The method of claim 18, further comprising:
applying a layer of chromium or titanium onto the polymer before depositing the metal coating.

* * * * *